(12) United States Patent
Kim et al.

(10) Patent No.: US 10,415,880 B2
(45) Date of Patent: Sep. 17, 2019

(54) HYBRID DRYING APPARATUS FOR HIGH OR MEDIUM VISCOSITY MATERIALS

(71) Applicant: KOREA INSTITUTE OF ENERGY RESEARCH, Daejeon (KR)

(72) Inventors: Sung Il Kim, Daejeon (KR); Sang Hyun Oh, Cheongju-si (KR); Ki Ho Park, Daejeon (KR)

(73) Assignee: Korea Institute of Energy Research, Daejeon (KR)

( * ) Notice: Subject to any disclaimer, the term of this patent is extended or adjusted under 35 U.S.C. 154(b) by 153 days.

(21) Appl. No.: 15/705,392

(22) Filed: Sep. 15, 2017

(65) Prior Publication Data

US 2018/0335257 A1    Nov. 22, 2018

(30) Foreign Application Priority Data

May 19, 2017 (KR) .................. 10-2017-0062088

(51) Int. Cl.
*D06F 58/00* (2006.01)
*F26B 1/00* (2006.01)
(Continued)

(52) U.S. Cl.
CPC .............. *F26B 1/00* (2013.01); *C12M 47/14* (2013.01); *F26B 3/04* (2013.01); *F26B 3/20* (2013.01);
(Continued)

(58) Field of Classification Search
CPC ...... F26B 17/008; F26B 21/02; F26B 17/003; F26B 3/20; F26B 1/00; C02F 11/18; C02F 11/12; B01D 29/072
See application file for complete search history.

(56) References Cited

U.S. PATENT DOCUMENTS 4,191,530 A * 3/1980 Bearce ...................... F26B 3/00
432/107
6,796,517 B1 * 9/2004 Pike ........................ B05C 11/08
239/548
(Continued)

FOREIGN PATENT DOCUMENTS

CN    204132333 U  *  2/2015
JP    2002-250589 A    9/2002
(Continued)

OTHER PUBLICATIONS

Korean Office Action dated Nov. 30, 2018.

*Primary Examiner* — Jason Lau
(74) *Attorney, Agent, or Firm* — Rabin & Berdo, P.C.

(57) ABSTRACT

A hybrid drying apparatus including: a bed portion having a horizontally disposed top surface; an object-to-be-dried supplying portion configured to spread an object to be dried on the top surface of the bed portion; and a driving unit configured to rotate and drive the bed portion or the object-to-be-dried supplying portion, wherein the object to be dried supplied from the object-to-be-dried supplying portion is spread on the top surface of the bed portion while the bed portion or the object-to-be-dried supplying portion is rotated, and the top surface of the bed portion is heated in such a manner that a lower portion of the bed portion is primarily heated so that the bed portion is used to dry the object to be dried coated on the top surface of the bed portion by the object-to-be-dried supplying portion.

13 Claims, 6 Drawing Sheets

(51) Int. Cl.
*C12M 1/00* (2006.01)
*F26B 3/20* (2006.01)
*F26B 11/02* (2006.01)
*F26B 11/08* (2006.01)
*F26B 3/04* (2006.01)

(52) U.S. Cl.
CPC .......... *F26B 11/026* (2013.01); *F26B 11/028* (2013.01); *F26B 11/08* (2013.01); *F26B 2200/02* (2013.01)

(56) References Cited

U.S. PATENT DOCUMENTS

| | | | | |
|---|---|---|---|---|
| 2002/0060181 | A1* | 5/2002 | Schreiber | B01D 33/17 210/396 |
| 2012/0168424 | A1* | 7/2012 | Cai | F26B 15/18 219/391 |
| 2014/0048463 | A1* | 2/2014 | Weisselberg | F26B 17/003 210/149 |

FOREIGN PATENT DOCUMENTS

| | | |
|---|---|---|
| JP | 2007-113809 A | 5/2007 |
| KR | 10-2009-0052261 A | 5/2009 |
| KR | 10-1668781 B1 | 10/2016 |

* cited by examiner

HYBRID DRYING APPARATUS FOR HIGH OR MEDIUM VISCOSITY MATERIALS

CROSS-REFERENCE TO RELATED APPLICATION

This application claims priority to and the benefit of Korean Patent Application No. 2017-0062088 filed on May 19, 2017, the disclosure of which is incorporated herein by reference in its entirety.

BACKGROUND

1. Field of the Invention

The present invention relates to a hybrid drying apparatus for high or medium viscosity materials, and more particularly, to a hybrid drying apparatus for high or medium viscosity materials in which high or medium viscosity materials having medium viscosity or higher with relatively predetermined adhesion and viscosity can be dried.

2. Discussion of Related Art

Materials such as microalgae having fine particles with micrometer sizes, an aerogel paste, a total phosphorus sludge, and the like are medium viscosity materials (0.1 pa·s or higher) having no-drip viscosity like a liquid phase or high viscosity materials having higher viscosity. Moisture of the materials is removed by drying, and then usability thereof can be improved to be multipurpose. Thus, various drying apparatuses for high or medium viscosity materials have been developed.

For example, Japanese Patent Application No. 2001-47841 discloses a technology relating to a drying apparatus that dries viscous materials when the viscous materials move between agitation wings and are agitated by rotation of the agitation wings. However, in the drying apparatus, due to the rotation of the above-mentioned agitation wings, a material to be dried is adhered to the agitation wings such that a cleaning operation is periodically required or drying efficiency is decreased.

In order to prevent adherence of a material to be dried to the agitation wings, Japanese Patent Application No. 2005-303999 discloses a technology in which an agitation holder that can be freely rotated is additionally included inside a drying drum. However, when the agitation holder is additionally included in the drying drum, the agitation holder is freely rotated such that uniform control is difficult and efficiency of agitation, i.e., efficiency of drying, is decreased.

Furthermore, Korean Patent Registration No. 10-1668781 discloses a technology relating to a hybrid drying apparatus for high viscosity materials, whereby drying is performed by inducing adhesion of a material to an outer surface of a rotation cylinder. However, in the case of a material having relatively low viscosity, the material may flow along the outer surface of the rotation cylinder such that an object to be dried is limited.

PRIOR-ART DOCUMENT

Patent Document (Patent document 1) Japanese Patent Laid-open Publication No. 2002-250589

(Patent document 2) Japanese Patent Laid-open Publication No. 2007-113809

(Patent document 3) Korean Patent Registration No. 10-1668781

SUMMARY OF THE INVENTION

The present invention is directed to a hybrid drying apparatus for high or medium viscosity materials having improved drying efficiency in which both medium viscosity materials having relatively not-high viscosity and high viscosity materials can be more efficiently dried.

According to an aspect of the present invention, there is provided a hybrid drying apparatus including: a bed portion having a horizontally disposed top surface; an object-to-be-dried supplying portion configured to spread an object to be dried on the top surface of the bed portion; and a driving unit configured to rotate and drive the bed portion or the object-to-be-dried supplying portion, wherein the object to be dried supplied from the object-to-be-dried supplying portion is spread on the top surface of the bed portion while the bed portion or the object-to-be-dried supplying portion is rotated, and the top surface of the bed portion is heated in such a manner that a lower portion of the bed portion is primarily heated, so that the bed portion is used to dry the object to be dried spread on the top surface of the bed portion by the object-to-be-dried supplying portion.

The bed portion may have a circular plate shape.

The bed portion may have a rotation shaft provided in a center thereof, and the rotation shaft may be rotatably connected to the driving unit.

The hybrid drying apparatus may further include a lower jacket configured to cover a bottom surface of the bed portion and form a space portion for a flow of hot air between the bottom surface of the bed portion and the lower jacket and including a first inlet through which the hot air is introduced into the space portion and a first outlet through which the hot air is discharged to an outside of the space portion, wherein the bed portion is used to dry the object to be dried spread on the top surface of the bed portion via heat supplied to the bed portion due to the hot air introduced into the lower jacket.

A fin portion may be disposed inside the lower jacket and may include a plurality of heat transfer fins that extend to the bottom surface of the bed portion.

The rotation shaft may extend to a lower side of the bed portion, and the first inlet may be formed as a hollow portion that surrounds the rotation shaft, extends to a lower side of the lower jacket and extends to the bottom surface of the bed portion in the space portion, and the first outlet may be formed as an outer hollow portion that is disposed at the lower side of the low jacket, surrounds the hollow portion, and extends downwards.

The hybrid drying apparatus may further include an upper cover portion that covers a section of the bed portion which is spread with the object to be dried, and the upper cover portion may form an upper space on the top surface of the bed portion, wherein a second outlet may be provided in the upper cover portion so as to discharge a discharge gas generated from the object to be dried spread on the top surface of the bed portion.

A second inlet through which the hot air is introduced into an upper portion of the upper cover portion may be provided in the upper cover portion.

The hot air introduced from the second inlet of the upper cover portion may be the hot air discharged from the lower jacket.

The object-to-be-dried supplying portion may extend from a central portion of the top surface of the bed portion toward edges of the upper surface to provide the object to be dried to the top surface of the bed portion.

The object-to-be-dried supplying portion may extend from the central portion of the top surface of the bed portion toward the edges of the top surface and may include a slit through which the object to be dried is discharged.

The object-to-be-dried supplying portion may increase a quantity of the object to be dried supplied from the object-to-be-dried supplying portion nearer an outside of the bed portion from the central portion thereof.

The hybrid drying apparatus may further include a scraping unit disposed on the bed portion and configured to remove the object to be dried when the object to be dried is dried on the top surface of the bed portion from the top surface of the bed portion.

The scraping unit may be disposed on the top surface of the bed portion and may extend from s central portion of the top surface toward edges thereof.

The scraping unit may contact the top surface of the bed portion, contact the object to be dried of the top surface of the bed portion as the bed portion is rotated, remove the object to be dried from the top surface of the bed portion, and guide the object to be dried to be moved to an outside of the bed portion.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
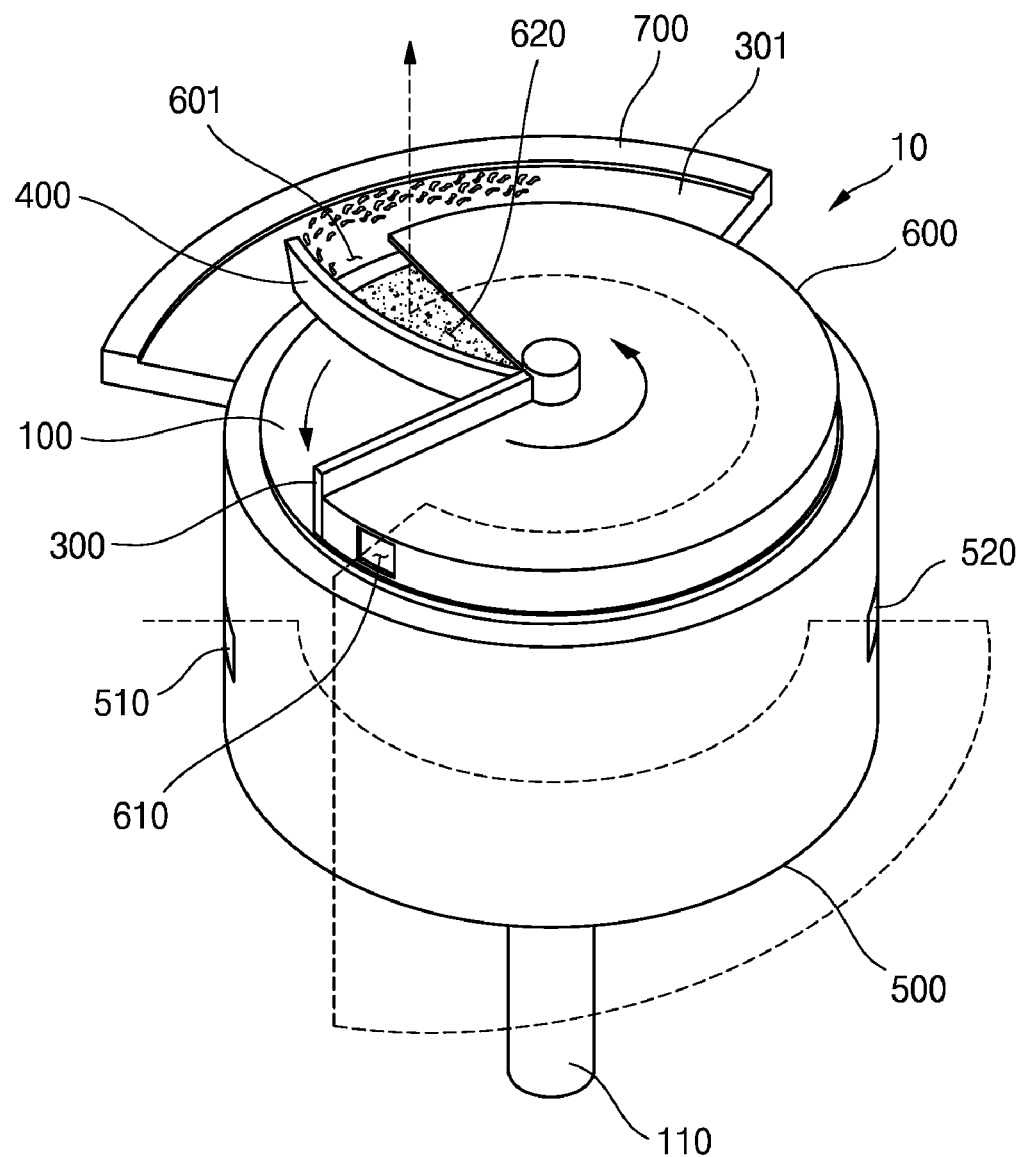
FIG. 1 is a perspective view of a hybrid drying apparatus according to an embodiment of the present invention.

The above and other advantages and a scheme for the advantages of the present invention will become readily apparent when considered in conjunction with the accompanying drawings with reference to the following detailed description. However, the scope of the present invention is not limited to such embodiments and the present invention may be realized in various forms. The embodiments which will be described below are only provided to bring the disclosure of the present invention to completion and assist those skilled in the art in completely understanding the present invention. The present invention is defined only by the scope of the appended claims. In addition, the same reference numerals are used to designate the same elements throughout the drawings.

It should be understood that although the terms first, second, third, etc. may be used herein to describe various elements, these elements are not limited by these terms. These terms are used to only distinguish one element, component, or section from another element, component, or section. The terminology used herein is for the purpose of describing particular embodiments only and is not intended to be limiting of the present inventive concept. As used herein, the singular forms "a," "an," and "the" are intended to include the plural forms as well unless clearly indicated otherwise by context.

It should be further understood that the terms "comprises" and/or "consists of" specify the presence of stated features, integers, steps, operations, elements, and/or components when used in this specification, but do not preclude the presence or addition of one or more other features, integers, steps, operations, elements, components, and/or groups thereof.

All terms (including technical and scientific terms) used herein have the same meanings as commonly understood by one of ordinary skill in the art to which this inventive concept belongs unless defined otherwise. It should be further understood that terms, such as those defined in commonly used dictionaries, should be interpreted as having a meaning that is consistent with their meaning in the context of the relevant art and are not to be interpreted in an idealized or overly formal sense unless expressly so defined herein.

Hereinafter, exemplary embodiments of the present invention will be described in detail with reference to the accompanying drawings.

Figure 2:
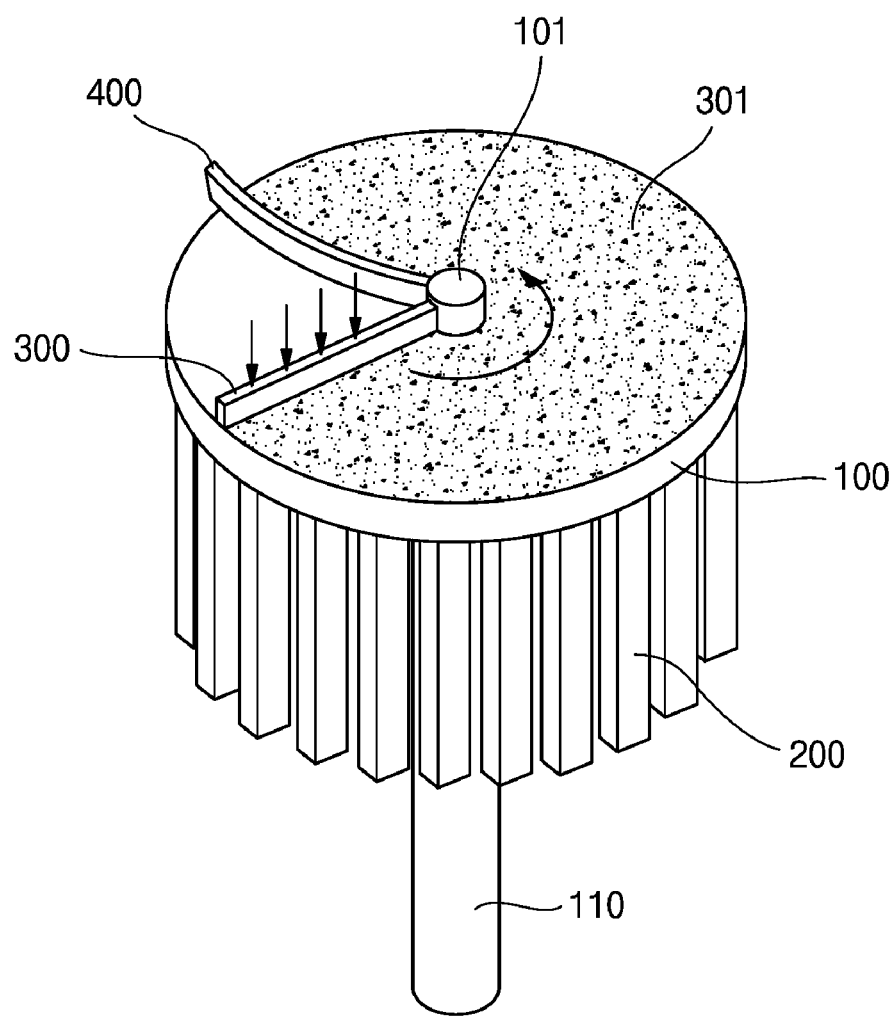
FIG. 2 is a perspective view of a state in which a lower jacket and an upper cover portion are removed in FIG. 1.
Figure 3:
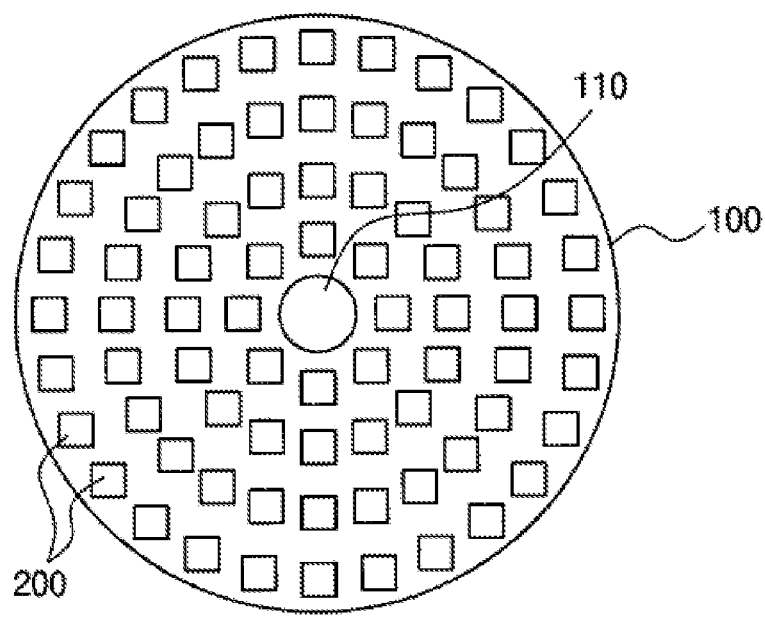
FIG. 3 is a bottom view of a bed portion of FIG. 1 in a downward direction.

FIG. 1 is a perspective view of a hybrid drying apparatus according to an embodiment of the present invention, FIG. 2 is a perspective view of a state in which a lower jacket and an upper cover portion are removed in FIG. 1, and FIG. 3 is a bottom view of a bed portion of FIG. 1 in a downward direction.

Referring to the drawings, a hybrid drying apparatus 10 according to an embodiment of the present invention includes a bed portion 100, a driving unit 115, an object-to-be-dried supplying portion 300, a scraping unit 400, a lower jacket 500, and an upper cover portion 600.

The bed portion 100 has a circular plate shape. A top surface of the bed portion 100 is horizontally disposed, and an object to be dried 301 is coated or spread thinly on the top surface of the bed portion 100.

In the present invention, the object to be dried 301 is a medium or high viscosity material. The medium viscosity material is defined as a material having viscosity higher than a no-drop viscosity like a liquid phase, and the high viscosity material is defined as a material having viscosity in which the high viscosity material with higher viscosity than that of the medium viscosity material is closely adhered to the surface of the object to be dried 301 and is nearly fixed thereto.

Because the top surface of the bed portion 100 is disposed in parallel to the ground, although the bed portion 100 is rotated by a rotation shaft 110, like in an embodiment of the present invention, when the object to be dried 301 coated on the bed portion 100 has higher viscosity than that of the medium viscosity material, the object to be dried 301 may not drop to the outside of the bed portion 100 but may be disposed on the top surface of the bed portion 100. Thus, the material having viscosity higher than medium viscosity may be efficiently dried on the bed portion 100.

According to an embodiment of the present invention, the rotation shaft 110 is provided in the center of the bed portion 100, and the bed portion 100 is rotated by rotation of the rotation shaft 110. The rotation shaft 110 extends toward a lower side of the bed portion 100 and is connected to a driving motor, which is the driving unit 115, and rotates.

According to another embodiment of the present invention, the bed portion 100 may be fixed, and the object-to-be dried supplying portion 300 and the scraping unit 400, which are disposed on the top surface of the bed portion 100, may be integrally rotated with the upper cover portion 600 with respect to the bed portion 100. In this case, the driving unit 115 may be connected to integrally rotate the object-to-be-dried supplying portion 300, the scraping unit 400, and the upper cover portion 600 with respect to the bed portion.

Hereinafter, the case in which the bed portion 100 is rotated according to an embodiment of the present invention will be described.

The object-to-be dried supplying portion 300 is disposed on the top surface of the bed portion 100 and spreads the object to be dried 301 on the surface of the bed portion 100.

Figure 5:
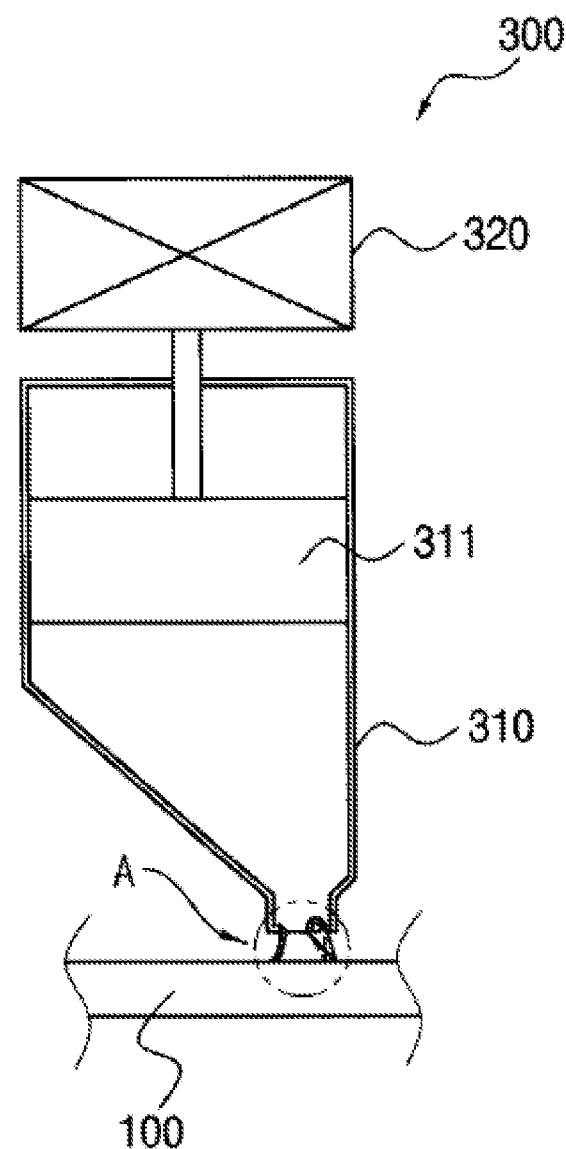
FIG. 5 is a cross-sectional view of an object-to-be-dried supplying portion of FIG. 1.
Figure 6:
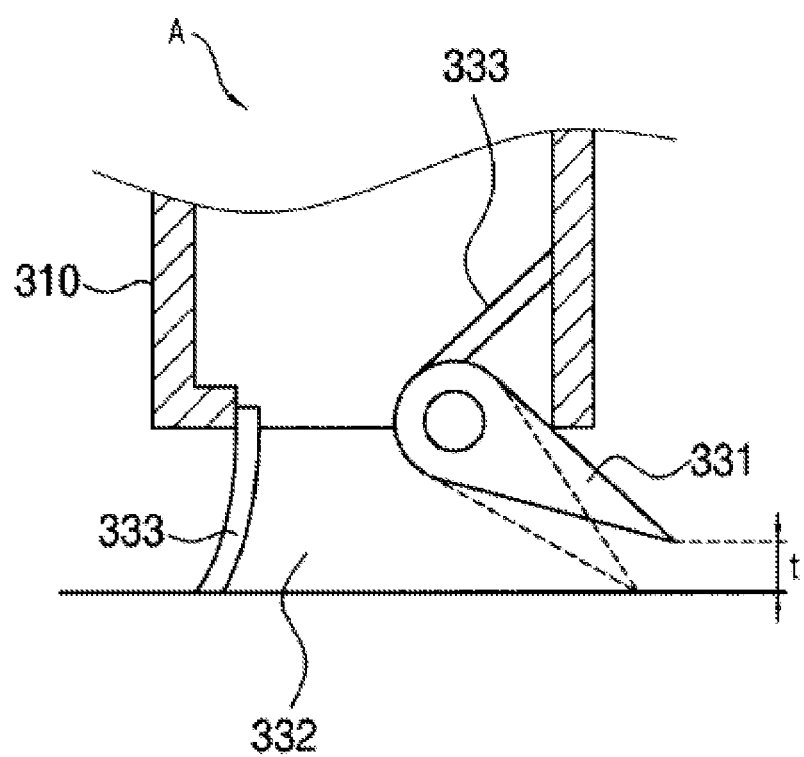
FIG. 6 is an enlarged view of portion A of FIG. 5.

FIGS. 5 and 6 are views of an object-to-be-dried supplying portion of a hybrid drying apparatus according to an embodiment of the present invention.

The object-to-be-dried supplying portion 300 includes an extruder 320, a hopper 310, a piston 311, a slit 332, and a nozzle portion 331, as illustrated in FIGS. 5 and 6.

The extruder 320 may extrude the object to be dried 301 and discharge the extruded object to be dried 301 to the hopper 310, and the object to be dried 301 may be coated on the top surface of the bed portion 100 through the slit 332 formed in a bottom end of the hopper 310.

The extruder 320 pushes the object to be dried 301 inside the hopper 310 into the slit 332 via the piston 311. In this case, because the object to be dried 310 disposed in the hopper 310 is a medium viscosity material or high viscosity material, an O-ring (not shown) may be formed inside the piston 311 such that the occurrence of rolling of the piston 311 is prevented and the object-to-be-dried 301 can be more efficiently transported.

The nozzle portion 331 is provided at one side of the slit 332 in a direction in which the object to be dried 301 is coated. The object to be dried 301 is coated on the top surface of the bed portion 100 through the nozzle portion 331. A distance t between the nozzle portion 331 and the top surface of the bed portion 100 is uniformly maintained when the object to be dried 301 is coated so that a thickness of the object to be dried 301 to be coated on the top surface of the bed portion 100 can be uniformly maintained. Also, the distance t is changed in various ways so that the thickness of the object to be dried 301 coated on the bed portion 100 can be changed to be different.

Meanwhile, a blocking layer 333 may be formed in the slit 332 to face the nozzle portion 331 and prevent leakage of the object to be dried 301 discharged through the slit 332 in other directions than a direction in which the nozzle portion 331 is disposed. The blocking layer 333 may be formed of silicon, Teflon, or the like. The blocking layer 333 may also perform a function of preventing movement of hot air supplied to the top surface of the bed portion 100 to the outside of the blocking layer 333.

The object-to-be-dried supplying portion 300 is disposed from a central portion 101 of the center of the top surface of the bed portion 100 toward edges of the top surface of the bed portion 100. For example, the object-to-be-dried supplying portion 300 may be disposed on the top surface of the bed portion 100 in a radial direction thereof. Thus, when the object to be dried 301 is extruded by the extruder 320 and the bed portion 100 is rotated by the rotation shaft 110 disposed in the center, the object to be dried 301 may be coated on the top surface of the bed portion 100 in the form of a thin layer.

Because a tangential speed is increased nearer to the edges of the bed portion 100 from the central portion 101 thereof when the bed portion 100 is rotated, the quantity of the object to be dried 301 to be coated on the bed portion 100 needs to be increased nearer to the edges of the bed portion 100 from the central portion 101 thereof. To this end, a width of the slit 332 may be increased nearer to the edges of the bed portion 100. Thus, the object to be dried 301 may be more uniformly coated on the top surface of the bed portion 100.

The scraping unit 400 is disposed on the top surface of the bed portion 100 adjacent to the object-to-be-dried supplying portion 300.

In order to maximally dry the object to be dried 301 coated on the top surface of the bed portion 100, the object to be dried 301 needs to be disposed on the top surface of the bed portion 100 for the longest time. Thus, when the bed portion 100 is rotated in a counterclockwise direction, as illustrated in FIGS. 1 and 2, the scraping unit 400 is preferably disposed closest to the object-to-be-dried supplying portion 300 in a clockwise direction based on the object-to-be-dried supplying portion 300.

The scraping unit 400 extends from the central portion 101 of the top surface of the bed portion 100 toward edges of the top surface thereof, like the object-to-be-dried supplying portion 300. For example, the scraping unit 400 may extend from the top surface of the bed portion 100 in the radial direction or a spiral direction. The scraping unit 400 is disposed to remove all of the object to be dried 301 on the top surface of the bed portion 100 when the bed portion 100 is rotated.

The scraping unit 400 includes a scraper that is disposed at a distal end of the scraping unit 400 contacting the top surface of the bed portion 100 to remove the object to be dried 301.

The object to be dried 301 to be removed from the top surface of the bed portion 100 using the scraping unit 400 is moved along the scraping unit 400 from the central portion 101 of the bed portion 100 to the outside, i.e., in a circumferential direction, and is discharged to the outside of the bed portion 100. An object-to-be dried discharge opening 601 through which the object to be dried 301 is discharged is disposed in a portion of the upper cover portion 600 in which a radial end of the scraping unit 400 is disposed.

The object to be dried 301 discharged to the outside of the bed portion 100 through the scraping unit 400 may be accommodated in an accommodation portion 700 placed outside the bed portion 100.

According to an embodiment of the present invention, a lower jacket 500 that covers a bottom surface of the bed portion 100 is provided in such a manner that a space portion 540 in which hot air is circulated can be formed. The space portion 540 inside the lower jacket 500 allows hot air which is introduced inside the lower jacket to heat the bottom surface of the bed portion 100. A fin portion 200 extending from the bottom surface of the base 100 may be disposed inside the lower jacket 500.

The fin portion 200 protrudes downward from the bottom surface of the bed portion 100 which is opposing side of a top surface on which the object to be dried 301 is spread. The fin portion 200 extends in a direction parallel to an extension direction of the rotation shaft 110, i.e., a direction perpendicular to the bed portion 100, by a predetermined length.

A plurality of fin portions 200 are arranged at regular intervals. The interval or arrangement of the plurality of fin portions 200 may be modified in various ways.

The fin portions 200 may be formed of a material having excellent thermal conductivity so that heat supplied into the lower jacket 500 can be effectively transferred to the bed portion 100.

Heat needs to be supplied to the fin portions 200 arranged in the center of the bottom surface of the bed portion 100 so that heat can be uniformly transferred to the bottom surface of the bed portion 100 through the fin portions 200. To this end, the plurality of fin portions 200 are preferably arranged so that a predetermined space can be formed therebetween.

In this way, according to an embodiment of the present invention, due to the heat supplied to the bed portion 100 through the fin portions 200, the object to be dried 301 coated on the top surface of the bed portion 100 can be more effectively dried. According to an embodiment of the present invention, the fin portions 200 are preferably provided. However, the use of various units that may improve heat transfer efficiency to the bed portion 100 is not excluded.

Figure 4:
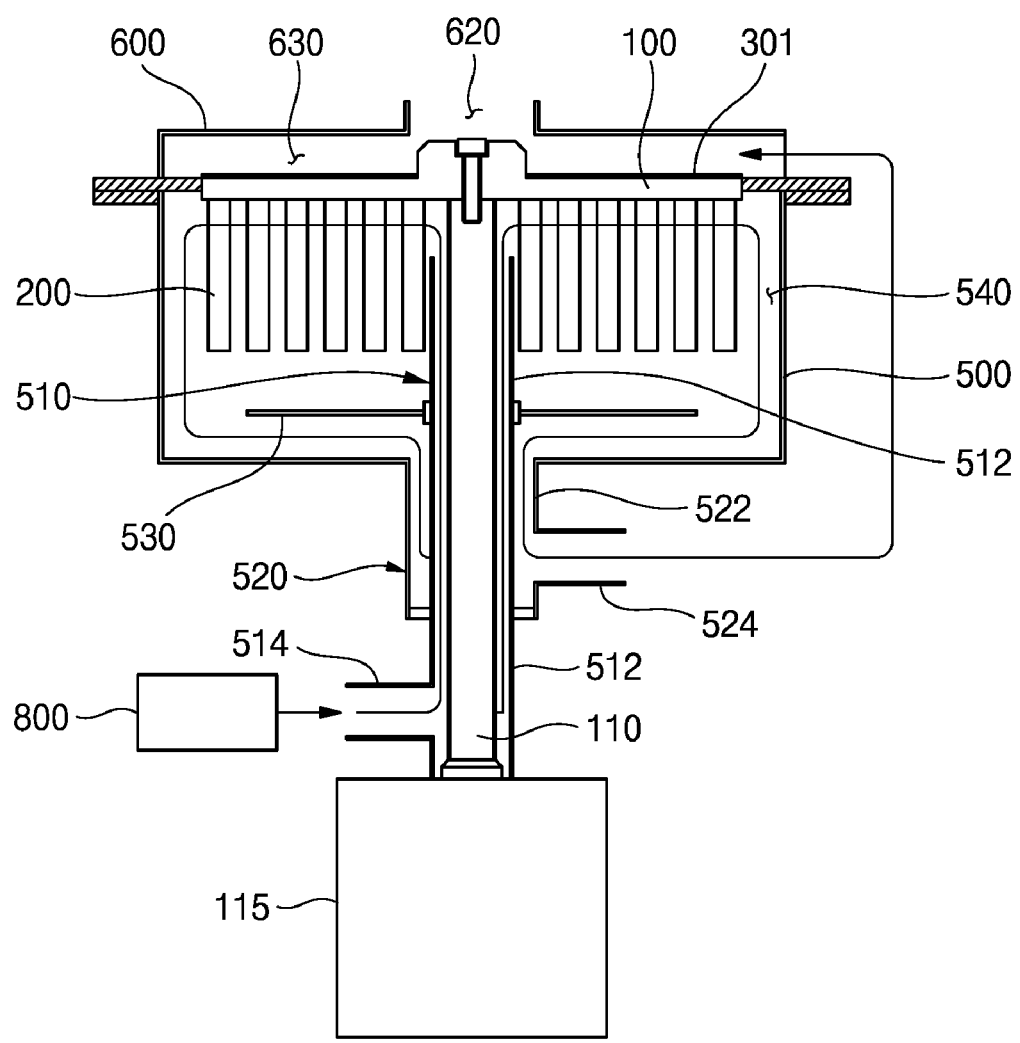
FIG. 4 is a cross-sectional view of a modified example of a hybrid drying apparatus according to an embodiment of the present invention.

As illustrated in FIGS. 1 and 4, the lower jacket 500 forms the space portion 540 which covers the bottom surface of the bed portion 100 and in which hot air for heating the bottom surface of the bed portion 100 is circulated.

The lower jacket 500 includes a first inlet 510 through which hot air is introduced from the outside and a first outlet 520 through which hot air is discharged to the outside. Due to the hot air introduced into the space portion 540 through the first inlet 510, heat is supplied to the bottom surface of the bed portion 100 and the fin portions 200 such that the object to be dried 301 spread on the top surface of the bed portion 100 can be dried.

According to the embodiment of the present invention illustrated in FIG. 1, the open first inlet 510 is formed in one side of the lower jacket 500 and a side opposite the first inlet 510 is open so that the first outlet 520 can be formed. Thus, hot air is introduced through the first inlet 510, passes through the fin portions 200 inside the lower jacket 500, and is then discharged through the first outlet 520. In this case, heat can be directly supplied to the bed portion 100.

FIG. 4 is a view of a modified example of a hybrid drying apparatus according to an embodiment of the present invention in which the first inlet 510 and the first outlet 520 are formed at the lower side of the lower jacket 500.

Referring to FIG. 4, the first inlet 510 includes a hollow portion 512 that surrounds the rotation shaft 110 of the bed portion 100 and extends along the rotation shaft 110.

The hollow portion 512 extends downward from a bottom end of the lower jacket 500 and extends from the space portion 540 inside the lower jacket 500 toward the bottom surface of the bed portion 100 upwards. Due to hot air introduced into the lower jacket 500 through the hollow portion 512, hot air is supplied to the bottom surface of the bed portion 100, flows in the radial direction along a space between the bottom surface of the bed portion 100 and the fin portions 200, and heats the bottom surface of the bed portion 100 and the fin portions 200. Thus, due to the hot air introduced into the lower jacket 500, heat can be more efficiently supplied to the bottom surface of the base 100 and the fin portions 200.

The rotation shaft 110 for rotating the bed portion 100 extends into the hollow portion 512, and the driving motor 115 for rotating the rotation shaft 110 is disposed at a bottom end of the hollow portion 512. Hot air is introduced into an introduction port 514 formed at one side of the hollow portion 512.

The hybrid drying apparatus according to the present invention may further include an air heating unit 800 that is connected to the introduction port 514 and heats and blows air introduced from the outside. The air heating unit 800 includes a heater and a fan for heating air.

The first outlet 520 includes an outer hollow portion 522 that is disposed at a bottom end of the lower jacket 500, surrounds the hollow portion 512, and extends downwards. The outer hollow portion 522 forms a path which communicates with the bottom end of the lower jacket 500 and through which the hot air introduced into the lower jacket 500 is discharged.

A disturbance plate 530 that protrudes outward from an outer circumferential surface of the hollow portion 512 may be provided in the space portion 540 inside the lower jacket 500 below the fin portions 200. Hot air discharged toward the bottom surface of the bed portion 100 through the hollow portion 512 by means of the disturbance plate 530 flows in the radial direction along a space between the bottom surface of the bed portion 100 and the fin portions 200, descends along the inner side of the lower jacket 500, and is introduced into the outer hollow portion 522 through a space between the disturbance plate 530 and the bottom surface of the lower jacket 500. Due to the disturbance plate 530, a flow distance of the hot air introduced into the lower jacket 500 is increased, and a stay time is increased so that heat transfer efficiency may be improved.

A discharge port 524 is formed at one side of the outer hollow portion 522 so that hot air may be discharged to the outside of the lower jacket 500. The discharge port 524 may be connected to a second inlet 610 formed in the upper cover portion 600, and hot air discharged from the lower jacket 500 may be supplied into the upper cover portion 600 and used to dry the object to be dried on the top surface of the base 100.

Referring to FIGS. 1 and 4, the hybrid drying apparatus according to the present invention includes the upper cover portion 600 that covers the top surface of the bed portion 100 to form an upper space 630 on the top surface of the bed portion 100.

Hot air is supplied into the upper space 630, and the object to be dried 301 spread on the top surface of the bed portion 100 may be directly dried using the hot air supplied into the upper space 630.

According to an embodiment of the present invention, hot air supplied into the upper space 630 is hot air provided from the lower jacket 500, and the hot air is reused so that energy efficiency may be improved.

According to an embodiment of the present invention, the above-described object-to-be dried supplying portion 300 and scraping unit 400 are disposed on the top surface of the bed portion 100, and the object to be dried 301 is spread in a section between the object-to-be-dried supplying portion 300 and the scraping unit 400 in a rotation direction of the bed portion 100. Thus, the upper cover portion 600 may also be formed to cover an object-to-be-dried coating section between the object-to-be-dried supplying portion 300 and the scraping unit 400, as illustrated in FIG. 1. Operations of the object-to-be-dried supplying portion 300 and the scraping unit 400 may be observed through a section in which no upper cover portion 600 is formed.

The second inlet 610 through which hot air is introduced into the upper space 630 toward one side of the upper cover portion 600, as illustrated in FIG. 1, is formed in the upper cover portion 600. As described above, the second inlet 610 is connected to the first outlet 520 so that hot air may flow through the second inlet 610 and the first outlet 520.

Also, a second outlet 620 through which the hot air passing through the upper space 630 is discharged is provided in the upper cover portion 600 so that the hot air passing through the upper space 630 may be discharged to the outside.

According to the embodiment of the present invention illustrated in FIG. 1, the second inlet 610 is formed in a position of a side adjacent to the object-to-be-dried supplying portion 300, and the second outlet 620 is formed in a position of the top surface adjacent to the scraping unit 400. However, embodiments of the present invention are not limited thereto. For example, both the second inlet 610 and the second outlet 620 may be formed in sides or a top surface of the upper cover portion 600. Also, as illustrated in FIG. 4, the second outlet 620 may be formed to surround the central portion 101 of the bed portion 100. Hot air introduced into the upper space 630 is used to directly dry the object to be dried 301 coated on the top surface of the base 10 and to discharge a discharge gas, such as moisture evaporated from the object to be dried 301, to the outside so that drying efficiency may be improved.

Hereinafter, an operation of the hybrid drying apparatus 10 and drying of the object to be dried 301 will be described with reference to FIG. 1.

First, regarding a flow path of hot air, hot air supplied from the outside is provided into the lower jacket 500 through the first inlet 510 of the lower jacket 500.

The hot air introduced through the first inlet 510 transfers heat to the bottom surface of the bed portion 100 disposed inside the lower jacket 500 and the fin portions 200 and is discharged to the outside of the lower jacket 500 through the first outlet 520. Due to the flow of hot air inside the lower jacket 500, the bed portion 100 is heated by the supplied heat, and the object to be dried 301 coated on the top surface of the bed portion 100 is dried using an indirect heating method.

Also, the hot air discharged through the first outlet 520 of the lower jacket 500 is introduced into the upper cover portion 600 through the second inlet 610 formed in one side of the upper cover portion 600.

The hot air introduced into the second inlet 610 flows into the upper space 630 inside the upper cover portion 600, directly dries the object to be dried 301 on the bed portion 100, and is discharged to the outside through the second outlet 602 formed in the other side of the upper cover portion 600 together with a discharge gas such as moisture evaporated from the object to be dried 301.

In terms of the flow of hot air in the operation of the hybrid drying apparatus, the object to be dried 301 is supplied from the object-to-be-dried supplying portion 300 and is coated on the top surface of the bed portion 100 while the bed portion 100 is rotated.

The object to be dried 301 coated on the top surface of the bed portion 100 is dried by heat supplied to the bed portion 100 by means of the lower jacket 500 at the lower side of the bed portion 100. Also, the object to be dried 301 is directly dried by the hot air supplied to the upper cover portion 600 from the lower jacket 500. Moisture generated during the drying of the object to be dried 301 is discharged to the outside due to the hot air so that drying is promoted.

A drying operation of the object to be dried 301 is performed simultaneously with rotation of the bed portion 100. The object to be dried 301 that is dried and reaches the scraping unit 400 due to rotation of the bed portion 100 is removed from the top surface of the bed portion 100 by means of the scraping unit 400, is guided by the scraping unit 400, and is discharged to the outside of the bed portion 100.

The object to be dried 301 discharged to the outside of the bed portion 100 is accommodated in the accommodation portion 700 and is collected later.

In an embodiment of the present invention described with reference to the drawings, the bed portion 100 is rotated by the rotation shaft 110, and the object-to-be-dried supplying portion 300 and the scraping unit 400 are fixed in a predetermined position of the top surface of the bed portion 100. However, the bed portion 100 may be fixed and the object-to-be-dried supplying portion 300 and the scraping unit 400 may be modified to be rotated together with the upper cover portion 600. Other embodiments of the present invention are included within the scope of the present invention. According to an embodiment of the present invention, the rotation of the bed portion 100 is advantageous for simplification of a structure.

According to an embodiment of the present invention, hot air is used to heat the bed portion 100 inside the lower jacket 500, is then introduced into the upper cover portion 600, and is reused, as described above, so that thermal energy of the hot air may be effectively utilized, and thus energy use efficiency is improved and the object to be dried 301 may be more efficiently dried.

According to an embodiment of the present invention, because drying is performed in a state in which the object to be dried is coated on the plate-shaped bed portion having a horizontally disposed top surface, an outflow of the object to be dried to the outside of the bed portion can be prevented so that an object to be dried having various viscosities from a medium viscosity material having relatively low viscosity to a high viscosity material can be more efficiently dried.

In addition, due to the hot air supplied by being passed through the lower jacket, the object to be dried can be more effectively dried by the hot air supplied to various positions of the object to be dried and heat can be effectively transferred to the object to be dried coated on the top surface of the bed portion through the fin portions that extend to the lower side of the bed portion.

In addition, because the bed portion has a circular plate shape and is rotated around the rotation shaft, heat supplied from the lower jacket can be relatively less lost and can be uniformly supplied to the object to be dried.

In addition, because hot air is supplied to the upper cover portion that covers the top surface of the bed portion, additional drying of the object to be dried on the bed portion can be performed so that drying performance can be improved. In particular, hot air applied to the upper cover portion is hot air that passes through the lower jacket and is re-circulated and introduced. Thus, energy efficiency can be improved.

In addition, the scraping unit that removes the object to be dried which is finished being dried is also disposed on the top surface of the bed portion so that the structure of the hybrid drying apparatus can be relatively simply designed and acquisition of the object to be dried can be effectively performed.

A hybrid drying apparatus for medium or high viscosity materials according to the present invention can be used in a drying apparatus for drying high or medium viscosity materials to recover the dried high or medium viscosity materials as an object to be dried.

According to embodiments of the present invention, because drying is performed in a state in which the object to be dried is coated on the plate-shaped bed portion, outflow of the object to be dried to the outside of the bed portion can be prevented so that the object to be dried having various viscosities from medium viscosity materials having relatively low viscosity to high viscosity materials can be more efficiently dried.

In addition, hot air supplied by being passed through the lower jacket is supplied to the object to be dried from various positions so that the object to be dried can be more efficiently dried.

In addition, heat is efficiently transferred to the object to be dried coated on the top surface of the bed portion through the fin portions that extend from the lower side of the bed portion so that drying performance can be improved.

In addition, when the bed portion having a circular plate shape is rotated around the rotation shaft, heat provided from the lower jacket can be relatively less lost and can be uniformly supplied to the object to be dried.

In addition, the upper jacket is formed on the top surface of the bed portion, and hot air is supplied to the object to be dried coated on the top surface of the bed portion through the upper jacket so that additional drying for the object to be dried can be performed, and thus drying performance can be improved. In particular, the hot air that passes through the lower jacket is introduced into the upper cover portion so that energy efficiency can be improved.

In addition, the scraping unit that removes the object to be dried which is finished being dried is disposed on the top surface of the bed portion so that the structure of the hybrid drying apparatus can be relatively simply designed and acquisition of the object to be dried can be efficiently performed.

It should be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A hybrid drying apparatus comprising:
   a bed portion having a horizontally disposed top surface;
   an object-to-be-dried supplying portion configured to spread an object to be dried on the top surface of the bed portion;
   a driving unit configured to rotate the bed portion or the object-to-be-dried supplying portion, wherein the object to be dried supplied from the object-to-be-dried supplying portion is spread on the top surface of the bed portion while the bed portion or the object-to-be-dried supplying portion is rotated by the driving unit;
   a scraping unit disposed on the bed portion and configured to remove the object to be dried when the object to be dried is dried on the top surface of the bed portion from the top surface of the bed portion;
   a lower jacket configured to cover a bottom surface of the bed portion and form a space portion for a flow of hot air between the bottom surface of the bed portion and the lower jacket and having a first inlet through which the hot air is introduced into the space portion and a first outlet through which the hot air is discharged to an outside of the space portion; and
   an upper cover portion configured to cover a section of the top surface which is coated with the object to be dried and form an upper space for the hot air on the top surface of the bed portion, the upper cover portion having a second inlet through which the hot air is introduced into the upper space and a second outlet through which a discharge gas generated from the object to be dried coated on the top surface during drying is discharged, wherein the second inlet is connected to the first outlet,
   wherein the hot air introduced into the space portion of the lower jacket heats the bottom surface of the bed portion to transfer heat to the object to be dried on the top surface on the bed portion without the contacting the object to be dried, and then the hot air discharged from the space portion of the lower jacket through the first outlet is introduced into the upper space of the upper cover portion through the second inlet and heat directly the object to be dried on the top surface of the bed portion.

2. The hybrid drying apparatus of claim 1, wherein the bed portion has a circular plate shape.

3. The hybrid drying apparatus of claim 2, wherein the bed portion is coupled to a rotation shaft provided in a center thereof, and the rotation shaft is rotatably connected to the driving unit.

4. The hybrid drying apparatus of claim 1, wherein a fin portion is disposed inside the lower jacket and comprises a plurality of heat transfer fins that extend to the bottom surface of the bed portion.

5. The hybrid drying apparatus of claim 3, wherein the rotation shaft extends to a lower side of the bed portion, and the first inlet is formed as a hollow portion that surrounds the rotation shaft, extends to a lower side of the lower jacket, and extends to the bottom surface of the bed portion in the space portion, and the first outlet is formed as an outer hollow portion that is disposed at the lower side of the low jacket, surrounds the hollow portion, and extends downwards.

6. The hybrid drying apparatus of claim 1, wherein the object-to-be-dried supplying portion extends from a central portion of the top surface of the bed portion toward edges of the upper surface to provide the object to be dried to the top surface of the bed portion.

7. The hybrid drying apparatus of claim 6, wherein the object-to-be-dried supplying portion extends from the central portion of the top surface of the bed portion toward the edges of the top surface and comprises a slit through which the object to be dried is discharged.

8. The hybrid drying apparatus of claim 6, wherein the object-to-be-dried supplying portion increases a quantity of the object to be dried supplied from the object-to-be-dried supplying portion nearer an outside of the bed portion from the central portion thereof.

9. The hybrid drying apparatus of claim 1, wherein the scraping unit is disposed on the top surface of the bed portion and extends from a central portion of the top surface toward edges thereof.

10. The hybrid drying apparatus of claim 9, wherein the scraping unit contacts the top surface of the bed portion, contacts the object to be dried on the top surface of the bed portion as the bed portion is rotated, removes the object to be dried from the top surface of the bed portion, and guides the object to be dried to be moved to an outside of the bed portion.

11. A hybrid drying apparatus comprising:
    a bed portion having a horizontally disposed top surface;
    an object-to-be-dried supplying portion configured to spread an object to be dried on the top surface of the bed portion; and
    a driving unit configured to rotate the bed portion, wherein the bed portion is coupled to a rotation shaft provided in a center thereof, and the rotation shaft is rotatably connected to the driving unit; and a lower jacket configured to cover a bottom surface of the bed portion and form a space portion for a flow of hot air between the bottom surface of the bed portion and the lower jacket and comprising a first inlet through which the hot air is introduced into the space portion and a first outlet through which the hot air is discharged to an outside of the space portion, wherein the bed portion is used to dry the object to be dried spread on the top surface of the bed portion via heat supplied to the bed portion due to the hot air introduced into the lower jacket, wherein the object to be dried supplied from the object-to-be-dried supplying portion is spread on the top surface of the bed portion while the bed portion is rotated;

wherein the top surface of the bed portion is heated in such a manner that a lower portion of the bed portion is heated to transfer heat to the top surface of the bed portion, such that the object to be dried spread on the top surface of the bed portion can be dried, and wherein the rotation shaft extends to a lower side of the bed portion, and the first inlet is formed as a hollow portion that surrounds the rotation shaft, extends to a lower side of the lower jacket, and extends to the bottom surface of the bed portion in the space portion, and the first outlet is formed as an outer hollow portion that is disposed at the lower side of the low jacket, surrounds the hollow portion, and extends downwards.

12. The hybrid drying apparatus of claim 11, wherein the object-to-be-dried supplying portion extends from the central portion of the top surface of the bed portion toward the edges of the top surface and comprises a slit through which the object to be dried is spread on the top surface of the bed portion, and wherein the slit includes a nozzle portion for allowing the object to be dried to be discharged on the top surface of the bed portion and a blocking layer disposed facing the nozzle portion to prevent leakage of the object to be dried discharged in other directions than a direction in which the nozzle portion is disposed.

13. The hybrid drying apparatus of claim 11, further comprising an upper cover portion that covers a section of the bed portion which is coated with the object to be dried, and the upper cover portion forms an upper space on the top surface of the bed portion, wherein a second outlet is provided in the upper cover portion to discharge a discharge gas generated from the object to be dried coated on the top surface of the bed portion, and wherein the hot air introduced into the space portion of the lower jacket heats the bottom surface of the bed portion to transfer heat to the object to be dried on the top surface on the bed portion without the contacting the object to be dried, and then the hot air discharged from the space portion of the lower jacket through the first outlet is introduced into the upper space of the upper cover portion through the second inlet and heat directly the object to be dried on the top surface of the bed portion.

* * * * *